United States Patent [19]
Bruckner et al.

[11] Patent Number: 6,102,300
[45] Date of Patent: Aug. 15, 2000

[54] AROMATHERAPY SCENT DISPENSER HAVING CASING WITH LIVING HINGE ATTACHED SNAP FIT LID

[76] Inventors: Tony A. Bruckner; James V. Bruckner; Robert F. Gurnsey, all of P.O. Box 297, Clinton, Ark. 72031

[21] Appl. No.: 09/303,858

[22] Filed: May 3, 1999

[51] Int. Cl.[7] .................................................. A24F 25/00
[52] U.S. Cl. .................. 239/55; 239/56; 239/57
[58] Field of Search .................. 239/53, 55, 56, 239/57, 58; 424/1.25, 40

[56] References Cited

U.S. PATENT DOCUMENTS

| | | | |
|---|---|---|---|
| 581,837 | 5/1897 | Walker | 239/54 |
| 1,732,028 | 10/1929 | Reiner | 239/54 |
| 1,954,893 | 4/1934 | Saeks | 239/54 |
| 2,109,092 | 2/1938 | Roll | 299/24 |
| 2,560,681 | 7/1951 | Berkowitz | 299/24 |
| 2,740,662 | 4/1956 | Scott | 299/55 |
| 3,784,102 | 1/1974 | Stults | 239/36 |
| 3,823,873 | 7/1974 | Miller et al. | 239/54 |
| 4,208,012 | 6/1980 | Dutcher | 239/57 |
| 4,374,571 | 2/1983 | Hirvela | 239/36 |
| 4,465,232 | 8/1984 | Field | 239/36 |
| 4,610,394 | 9/1986 | Bryson | 239/57 |
| 4,815,659 | 3/1989 | Turko et al. | 239/6 |
| 4,839,144 | 6/1989 | Martin | 422/305 |
| 4,938,419 | 7/1990 | Weick | 239/55 |
| 4,960,240 | 10/1990 | McElfresh | 239/56 |
| 5,460,787 | 10/1995 | Colon | 422/123 |

FOREIGN PATENT DOCUMENTS 1398071  6/1975  United Kingdom ............... 239/55

*Primary Examiner*—Lesley D. Morris
*Assistant Examiner*—Jorge Bocanegra
*Attorney, Agent, or Firm*—Flanagan & Flanagan; John K. Flanagan; John R. Flanagan

[57] ABSTRACT

A pocket size aromatherapy scent dispenser includes a flat casing defining a narrow cavity, a lid formed by an upper portion of the casing and a living hinge extending across the casing below the upper portion and pivotally connecting the lid to a remainder portion of the casing such that the lid can pivot about the living hinge between opened and closed positions relative to the remainder portion of the casing. The lid in the opened position is pivoted away from the remainder portion of the casing and opens an upper portion of the narrow cavity above the living hinge to an external environment. The lid in the closed position is disposed adjacent to the remainder portion of the casing and closes the upper portion of the cavity to the external environment. A piece of absorbent material carrying an aroma-producing substance is contained within the narrow cavity and has an upper portion partially exposed to the external environment when the lid is in the opened position such that a scent is produced that escapes to the external environment. A flat insert plate is disposed within narrow the cavity of the casing and contacts the upper portion of the piece of material. The insert plate partially exposes the upper portion of the piece of material to the external environment when the lid is in the opened position.

12 Claims, 3 Drawing Sheets

AROMATHERAPY SCENT DISPENSER HAVING CASING WITH LIVING HINGE ATTACHED SNAP FIT LID

BACKGROUND OF THE INVENTION

1. Field of the Invention

The present invention generally relates to devices carrying odoriferous material for dispensing scents and, more particularly, is concerned with a pocket size aromatherapy scent dispenser having a casing with an upper portion forming a living hinge attached snap fit lid.

2. Description of the Prior Art

Aromatherapy is a natural, drug-free treatment for the human body which has been found to be significantly effective in relieving the discomforts of many health-related complaints. Aromatherapy is derived from an ancient practice of using natural plant essences to treat illness and enhance health. This ancient practice uses pure essential oils extracted from a wide assortment of natural botanicals. It is believed that these oils found in plants, flowers, fruit, bark and roots provide scents that can restore a healthy balance of the body, mind and spirit.

When aromatic molecules are inhaled, they are believed to make contact with nerve-receptacle bundles found at the top of the nasal cavity. When the aromatic essence contacts these nerves, they send signals that result in brain activity. These responses have been observed through brain scans and other diagnostic technologies. Aromatherapy applies to the delicate blending of these oils to treat specific symptoms. Each individual essence has distinct therapeutic qualities.

Various devices have been developed over the years for use in aromatherapy. Representative examples of such devices and the like are disclosed in U.S. Pat. No. 581,837 to Walker, U.S. Pat. No. 1,732,028 to Reiner, U.S. Pat. No. 2,109,092 to Roll, U.S. Pat. No. 2,560,681 to Berkowitz, U.S. Pat. No. 2,740,662 to Scott, U.S. Pat. No. 3,784,102 to Stults, U.S. Pat. No. 4,374,571 to Hirvela, U.S. Pat. No. 4,465,232 to Field, U.S. Pat. No. 4,938,419 to Weick, U.S. Pat. No. 5,460,787 to Colon and European Pat. Nos. 16,015 and 322,452 to Weick.

The device of U.S. Pat. No. 4,938,419 to Weick, in particular, is for the atomizing of active substances of a paramedicinal or cosmetic nature. The Weick device includes a plate-form flat hollow body having first and second parts. The first part encloses an atomizing chamber. The second part has a reserve chamber of an active substance. The chambers are separated by a transverse wall which has channels through which lead wick-type conductors of the active substance extending at upper zones into a tampon and at lower zones into the atomizing chamber. One of two side walls of the first part is porous. A slide-type cover element is provided to cover the first part. The body has a push-in sealing groove open toward the cover element. The cover element may engage a rim section in the push-in sealing groove in a closed position. A problem exists, however, with the Weick device in that it is a complex package with many parts.

Consequently, a need remains for an aromatherapy scent dispenser which will provide a more simple and yet still effective package for providing aromatherapy scents without introducing any new drawbacks over that of the prior art.

SUMMARY OF THE INVENTION

The present invention provides a pocket size aromatherapy scent dispenser designed to satisfy the aforementioned need. The pocket size aromatherapy scent dispenser of the present invention is simple, compact and effective, and employs a minimum number of parts. In particular, the scent dispenser has a flat elongated casing with a flat piece of absorbent material carrying an aroma-producing substance being contained in a narrow cavity of the casing and an upper portion of the casing forming a lid attached by a living hinge to the remainder of the casing and pivotal relative thereto between opened and closed positions. The scent dispenser also has a flat insert plate contacting an upper portion of the piece of absorbent material and partially exposing the same when the lid is pivoted to the opened position.

Accordingly, the present invention is directed to a pocket size aromatherapy scent dispenser which comprises: (a) an elongated flat casing defining a narrow cavity therein and having an upper portion and a remainder portion; (b) a lid formed by the upper portion of the casing and a living hinge extending transversely across the casing below the upper portion and pivotally connecting the upper portion to the remainder portion of the casing such that the lid can undergo pivotal movement about the living hinge between an opened position and a closed position relative to the remainder portion of the casing, the lid in the opened position being pivoted away from the remainder portion of the casing and opening an upper portion of the narrow cavity of the casing above the living hinge to an external environment, the lid in the closed position being disposed adjacent to the remainder portion of the casing and closing the upper portion of the narrow cavity of the casing to the external environment; and (c) a body of material contained within the narrow cavity of the casing and carrying an aroma-producing substance, the body of material having an upper portion partially exposed to the external environment when the lid is in the opened position such that the aroma-producing substance on the body of material produces a scent that escapes to the external environment. The lid has a periphery with an arcuate shape. The body of material in the narrow cavity of the casing is a piece of absorbent material.

The dispenser also comprises interengaging means defined on the upper portion of the casing and the remainder portion thereof adjacent to the upper portion for making a releasable snap fit engagement of the lid with the remainder portion of the casing. The interengaging means includes a peripheral lip defined on the upper portion of the casing that forms the lid and a recessed peripheral edge defined on the remainder portion of the casing adjacent to the upper portion such that when the lid is in the closed position the recessed peripheral edge is adapted to make the snap fit engagement with the peripheral lip of the lid. The interengaging means further includes a protuberance formed on and extending upwardly from the recessed peripheral edge of the remainder portion of the casing. The protuberance is disposed behind the peripheral lip when the lid is in the closed position.

The dispenser further comprises a flat insert plate disposed within the narrow cavity of the casing. The insert plate contacts the upper portion of the body of material and partially exposes the upper portion of the body of material to the external environment when the lid is pivoted to the opened position. The insert plate has a plurality of apertures formed therethrough for passage of the scent of the substance carried by the body of material to the external environment when the lid is in the opened position. Further, the upper portion of the back wall of the casing has a pair of positioning pins attached thereon and extending into the cavity. The insert plate has a pair of holes spaced apart from one another and alignable with the positioning pins to match and snugly receive the positioning pins and thereby removably secure the insert plate to the upper portion of the back wall of the casing with the upper portion of the piece of material sandwiched therebetween such that the piece of material is exposed to the external environment substantially only through the apertures of the insert plate when the lid is in the opened position.

More particularly, the flat casing has a pair of opposite front and back walls. The narrow cavity is defined in the casing between the front and back walls. The front and back walls each has upper and lower portions. The lid is formed by the upper portion of the front wall with the living hinge extending thereacross between and pivotally connecting the upper and lower portions of the front wall such that in the opened position the lid is pivoted away from the upper portion of the back wall while in the closed position the lid is disposed adjacent to the upper portion of the back wall. The front and back walls of the casing have respective peripheral rims along which the lower portions of the front and back walls are sealably attached to one another so as to seal the narrow cavity extending below the living hinge and between the lower portions of the front and back walls. The lower portions of the front and back walls also have pluralities of pins and receptacles attached on interior surfaces thereof and spaced apart from one another along the peripheral rims of the front and back walls so as to align and place the peripheral rims of the front and back walls in contact with one another.

Additionally, the upper and lower portions of the back wall of the casing have a plurality of interior pins attached thereon and extending into the cavity and spaced apart so as to properly position the piece of material within the cavity.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which.

DETAILED DESCRIPTION OF THE INVENTION

Figure 1:
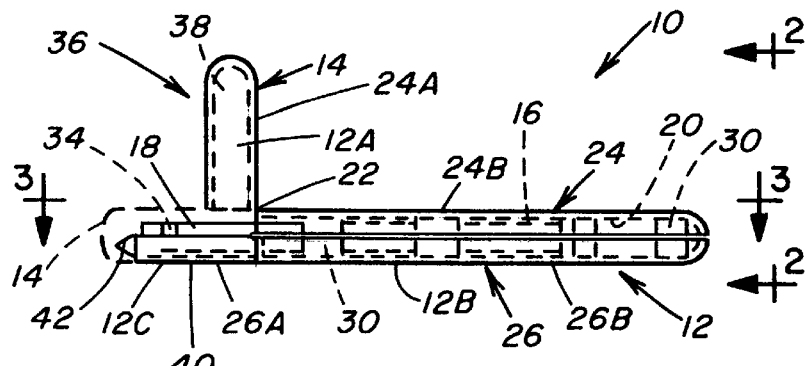
FIG. 1 is a side elevational view of the aromatherapy scent dispenser of the present invention showing a lid of the dispenser in opened and closed positions relative to a casing thereof.
Figure 2:
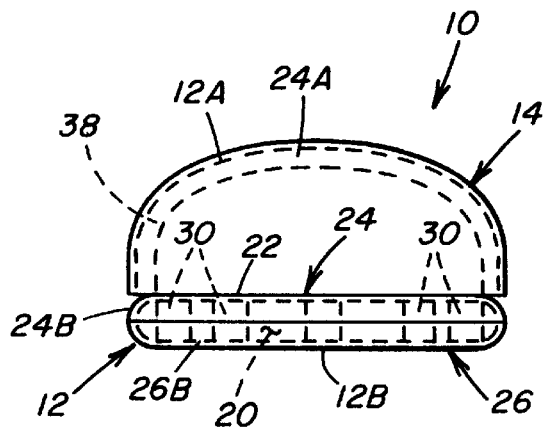
FIG. 2 is a bottom end elevational view of the dispenser as seen along line 2—2 of FIG. 1.
Figure 3:
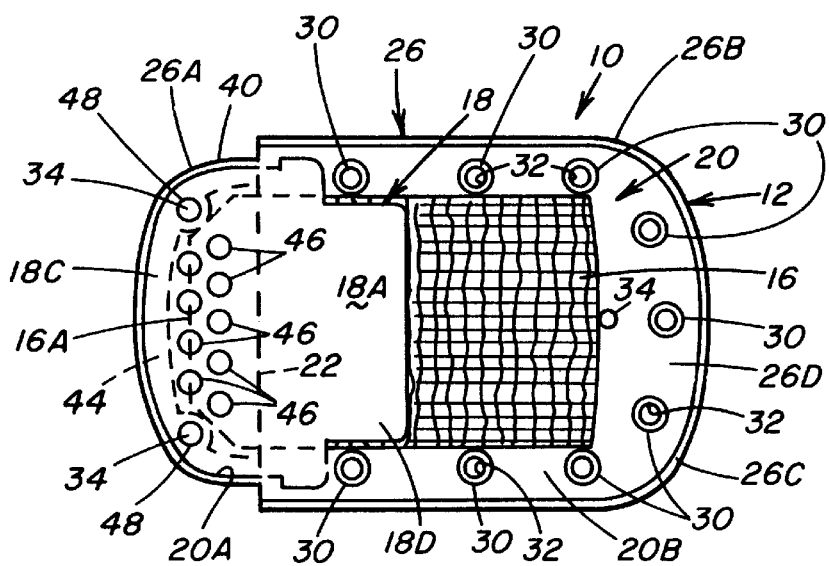
FIG. 3 is a front plan view of the dispenser as seen along line 3—3 of FIG. 1 with the lid and a front wall of the casing removed to fully show an insert plate and a piece of absorbent material of the dispenser.
Figure 5:
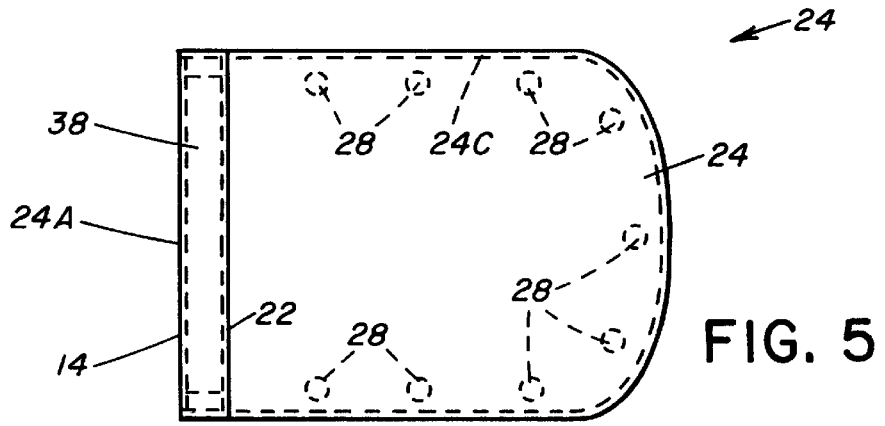
FIG. 5 is a top plan view of the front wall and lid of the dispenser casing as seen along line 5—5 of FIG. 4.
Figure 4:
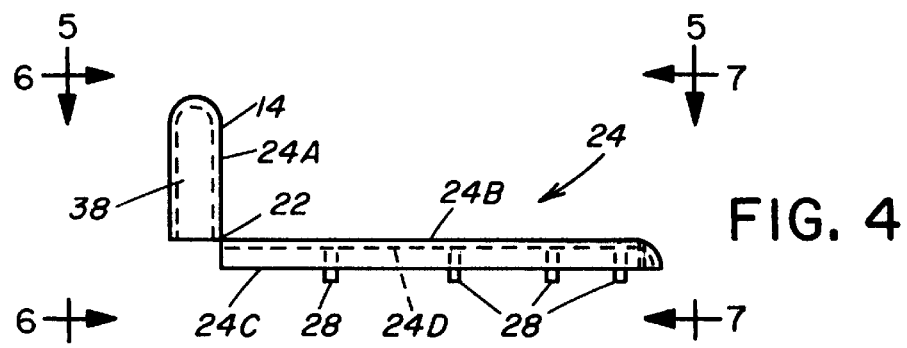
FIG. 4 is a side elevational view of the front wall of the casing of FIG. 1 with the lid in the opened position.
Figure 6:
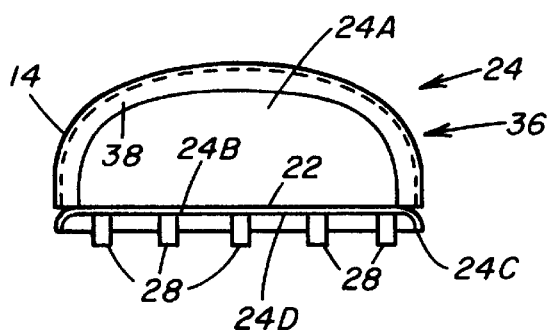
FIG. 6 is a top end elevational view of the front wall and lid of the dispenser as seen along line 6—6 of FIG. 4.
Figure 7:
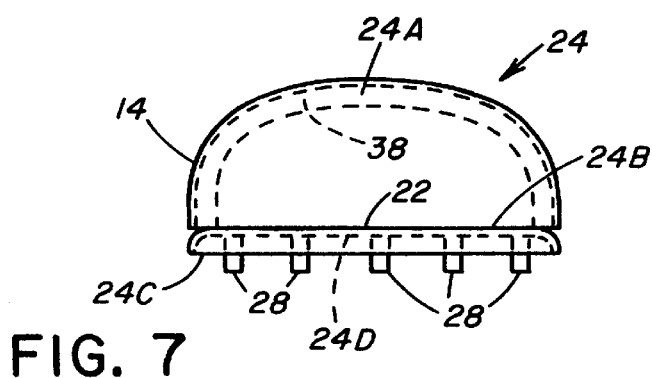
FIG. 7 is a bottom end elevational view of the front wall and lid of the dispenser as seen along line 7—7 of FIG. 4.

Referring to the drawings and particularly to FIGS. 1 to 3, there is illustrated a pocket size aromatherapy scent dispenser, generally designated 10, of the present invention. Basically, the aromatherapy scent dispenser 10 includes an elongated flat casing 12, a lid 14, a flat body of material 16 and an insert plate 18. The flat casing 12 defines a narrow cavity 20 therein. The lid 14 is formed by an upper portion 12A of the casing 12 and a living hinge 22 extending across the casing 12 below the upper portion 12A thereof and pivotally connecting the lid 14 to a remainder portion 12B of the casing 12 such that the lid 14 can pivot about the living hinge 22 between opened and closed positions, as respectively shown in solid line form and dashed line form in FIG. 1, relative to the remainder portion 12B of the casing 12. To reach the opened position, the lid 14 is pivoted away from the remainder portion 12B of the casing 12 and opens an upper portion 20A of the narrow cavity 20 above the living hinge 22 to an external environment. When moved to the closed position, the lid 14 is disposed adjacent to an upper portion 12C of the remainder portion 12B of the casing 12 and closes the upper portion 20A of the narrow cavity 20 to the external environment. The body of material 16 preferably is in the form of a piece of absorbent material carrying an aroma-producing substance. The piece of absorbent material 16 is contained within the narrow cavity 20 of the casing 12 and has an upper portion 16A partially exposed to the external environment when the lid 14 is in the opened position such that an aroma or scent is produced that escapes to the external environment. The insert plate 18 is disposed within the narrow cavity 20 of the casing 12 and contacts the upper portion 16A of the piece of material 16. The insert plate 18 also partially exposes the upper portion 16A of the piece of material 16 to the external environment when the lid 14 is in the opened position.

Referring now to FIGS. 1 to 11, the casing 12 is formed by a pair of opposite front and back walls 24, 26. Each of the front and back walls 24, 26 has an upper portion 24A, 26A and a lower portion 24B, 26B. The front and back walls 24, 26 have respective peripheral rims 24C, 26C which extend outwardly from the interior surfaces 24D, 26D of the front and back walls 24, 26 so as to define the narrow cavity 20 within the casing 12 between the front and back walls 24, 26 thereof. The lower portions 24B, 26B of the front and back walls 24, 26 are sealably attached to one another, such as by application of a suitable adhesive, along the peripheral rims 24C, 26C so as to seal a lower portion 20B of the narrow cavity 20 extending below the living hinge 22 between the lower portions 24B, 26B of the front and back walls 24, 26. The casing 12 and cavity 20 formed by the front and back walls 24, 26 have a substantially oblong configuration with the sizes of the lower portions 24B, 26B being substantially greater than the sizes of the upper portions 24A, 26A.

The lower portions 24B, 26B of the front and back walls 24, 26 also have pluralities of alignment pins 28 and hollow tubular-shaped receptacles 30 attached on and protruding outward from interior surfaces 24D, 26D thereof and disposed adjacent to the respective rims 24C, 26C of the front and back walls 24, 26. The alignment pins 28 and receptacles 30 are substantially cylindrical in shape and the pins 28 have diameters slightly smaller than the diameters of the bores 32 of the receptacles 30 such that the pins 28 will snugly fit within the bores 32 of the receptacles 30. The alignment pins 28 and receptacles 30 have heights relative to the interior surfaces 24D, 26D of the front and back walls 24, 26 the same as one another and greater than the heights of the rims 24C, 26C thereon. The alignment pins 28 and receptacles 30 thus extend outwardly past the rims 24C, 26C and in the respective pluralities thereof are spaced apart from one another and disposed along the rims 24C, 26C of the front and back walls 24, 26 such that the pins 28 pair with and fit into the receptacles 30 so as to align and place the rims 24C, 26C of the front and back walls 24, 26 in contact with one another. In addition, the upper and lower portions 26A, 26B of the back wall 26 of the casing 12 have a plurality of positioning pins 34 attached on the interior surface 26D of the back wall 26. The positioning pins 34 have about the same heights as the alignment pins 28 and protrude across the cavity 20 and are spaced apart so as to properly position the piece of material 16 within the cavity 20.

Referring to FIGS. 1 to 7, as described above the lid 14 is formed by the upper portion 24A of the front wall 24 of the casing 12 and is pivotable between the opened and closed position, as shown in solid and dashed line forms in FIG. 1, at and relative to the living hinge 22. The lid 14 has an arcuate shaped peripheral configuration. The lid 14 in the closed position is disposed adjacent to the upper portion 26A of the back wall 26 and closes the upper portion 20A oft the narrow cavity 20 of the body 12. The lid 14 in the opened position is angularly disposed away from the upper portion 26A of the back wall 26 and opens the upper portion 20A of the narrow cavity 20 of the casing 12 to the external environment. The piece of absorbent material 16 is removably captured within the narrow cavity 20 of the body 12 and is partially exposed at its upper portion 16A to the external environment when the lid 14 is in the opened position. The piece of absorbent material 16 is soaked or ladened with or otherwise carries a substance that can produce an aroma or scent believed to have beneficial effects on reducing pain associated with various conditions of users. Such substance can be any one of a plurality of well-known aromatherapy oils whose respective aromas or scents provide any of a variety of therapeutic benefits, including but not limited to stress, sinus, headache and mental and physical exhaustion relief. The aroma or scent of the substance is escapable from the narrow cavity 20 of the casing 12 to the external environment when the lid 14 is in the opened position.

Figures 9, 10, 11:
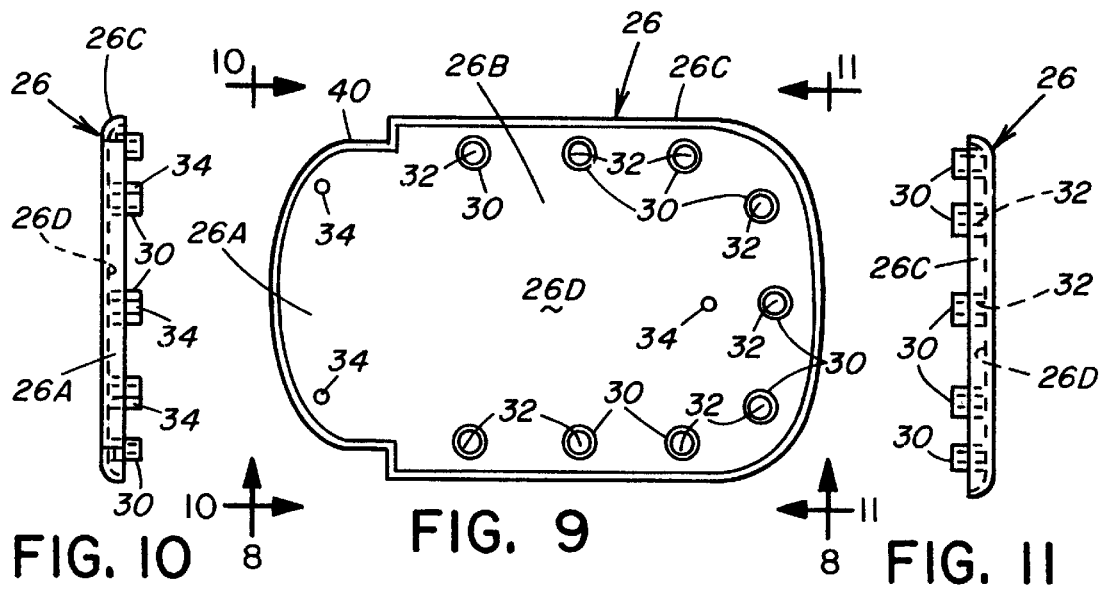
FIG. 9 is a top plan view of the back wall of the casing of the dispenser as seen along line 9—9 of FIG. 8.
FIG. 10 is a top end elevational view of the back wall of the dispenser as seen along line 10—10 of FIG. 9.
FIG. 11 is a bottom end elevational view of the back wall of the dispenser as seen along line 11—11 of FIG. 9.
Figure 8:
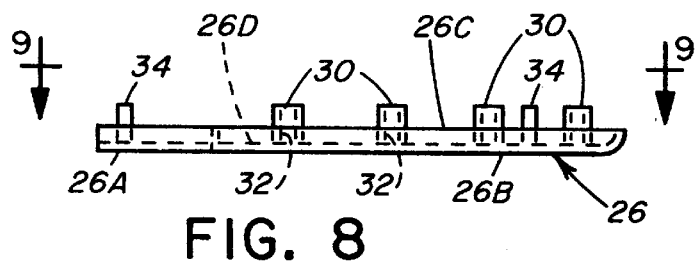
FIG. 8 is a side elevational view of a back wall of the casing of the dispenser of FIG. 1.

The dispenser 10 also comprises interengaging means 36 defined on the upper portions 24A, 26A of the front and back walls 24, 26 of the casing 12 for making a releasable snap fit engagement of the upper portion 24A of the front wall 24 forming the lid 14 with the upper portion 26A of the back wall 26. The interengaging means 36 includes a peripheral lip 38 defined on the upper portion 24A of the front wall 24 and thus on the lid 14 and a recessed peripheral edge 40 defined on the upper portion 26A of the back wall 26 adjacent to and facing toward the upper portion 24A of the front wall 24 such that when the lid 14 is in the closed position the recessed peripheral edge 40 is adapted to make the snap fit engagement with the peripheral lip 38 of the lid 14. As can be seen in FIGS. 3 and 9, the recessed peripheral edge 40 of the upper portion 26A of the back wall 26 is offset inwardly from the peripheral rim 26C of the lower portion 24B thereof. The interengaging means 36 further includes a protuberance 42 formed on and extending upwardly from the recessed peripheral edge 40 of the upper portion 26A of the back wall 26. The protuberance 42 is disposed behind the peripheral lip 38 when the lid 14 is in the closed position. The protuberance 42 thus enhances the snap fitting of the peripheral lip 38 of the lid 14 with the recessed peripheral edge 40 of the back wall 26.

Figure 13:
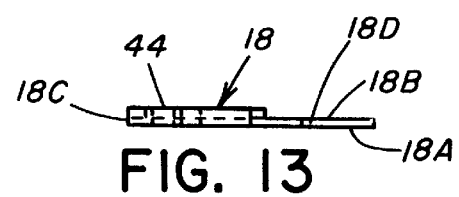
FIG. 13 is a side elevational view of the insert plate as seen along line 13—13 of FIG. 12.
Figure 12:
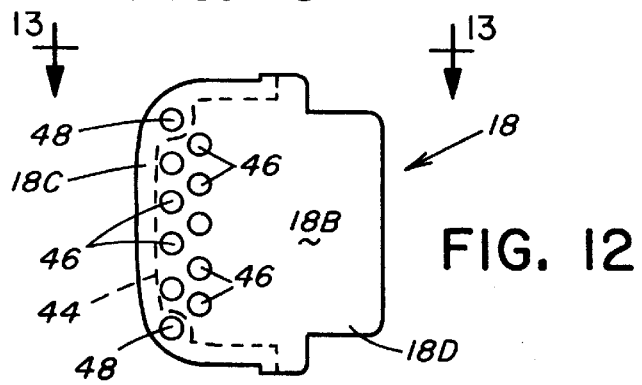
FIG. 12 is a front plan view of the insert plate removed from the dispenser.

Referring to FIGS. 3, 12 and 13, the flat insert plate 18 of the dispenser 10 is disposed within the narrow cavity of the casing. The insert plate 18 contacts the upper portion 16A of the piece of material 16 and partially exposes the upper portion 16A thereof to the external environment when the lid 14 is pivoted to the opened position. More particularly, the insert plate 18 has opposite first and second surfaces 18A, 18B. When the insert plate 18 is correctly disposed in the narrow cavity 20, the first surface 18A faces toward the upper portion 24A of the front wall 24 which forms the lid 14 while the second surface 18B faces toward the upper portion 26A of the back wall 26 of the casing 12. An upper portion 18C of the insert plate 18 is greater is size (length and width) than a lower portion 18D thereof such that the periphery of lower portion 18D is offset inwardly from the periphery of the upper portion 18C. The upper portion 18C has a generally arcuate configuration conforming to the configuration of the upper portion 26A of the back wall 26. The upper portion 18C has a peripheral rim 44 extending along the second surface 18B of the insert plate 18. When the insert plate 18 is disposed over the piece of material 16, the peripheral rim 44 rests on the peripheral rim 26C of the upper portion 26A of the back wall and surrounds the upper portion 16A of the piece of material 16.

The upper portion 18C of the insert plate 18 also has a plurality of apertures 46 formed therethrough in two rows adjacent to the rim 44 of the insert plate 18 for passage of the scent of the substance carried by the piece of material 16 to the external environment when the lid 14 is in the opened position. The insert plate 18 also has a pair of holes 48 at upper rounded corners of the peripheral rim 44 of the insert plate 18 which are spaced apart from one another and alignable with a pair of the positioning pins 34 on the upper portion 26A of the back wall 26 of the casing 12. The holes 48 are matched with and snugly receive the pair of positioning pins 34 so as to thereby removably secure the insert plate 18 to the upper portion 26A of the back wall 26 of the casing 12 with the upper portion 16A of the piece of material 16 sandwiched therebetween such that the piece of material 16 is partially exposed to the external environment substantially only through the apertures 46 of the insert plate 18 when the lid 14 is in the opened position. Each aperture 46 has a substantially circular configuration although it could have other configurations.

The piece of absorbent material 16 has a substantially rectangular configuration with its upper corners cut off at an angle to allow for the presence of the pair of positioning pins 34 that insert into the holes 48 of the insert plate 18. The aroma or scent is to be inhaled when the lid 14 is in the opened position. The opened upper portion 12A of the casing 12 should be placed adjacent to each nostril of the nose of the user without touching the skin of a user. The user should inhale slowly and deeply four to six times at each nostril while blocking the other nostril. The user may repeat, if necessary, after five minutes. The user may also follow any other suitable procedure for using the dispenser 10.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

We claim:

1. An aromatherapy scent dispenser, comprising:
   (a) an elongated flat casing having a pair of opposite front and back walls and a narrow cavity defined in said casing between said front and back walls, said front and back walls each having upper and lower portions;
   (b) a lid formed by said upper portion of said front wall of said casing and a living hinge extending transversely across said front wall and pivotally connecting said upper portion of said front wall to said lower portion thereof such that said lid can undergo pivotal movement about said living hinge between an opened position and a closed position relative to said upper portion of said back wall of said casing, said lid in said opened position being pivoted away from said upper portion of said back wall and opening an upper portion of said narrow cavity of said casing above said living hinge to an external environment, said lid in said closed position being disposed adjacent to said upper portion of said back wall and closing said upper portion of said narrow cavity of said casing to the external environment; and
   (c) aroma-producing means contained within said narrow cavity of said casing for producing a scent that escapes to the external environment when said lid is in said opened position.

2. The dispenser of claim 1 wherein said lower portions of said front and back walls of said casing have respective peripheral rims along which said lower portions of said front and back walls are sealably attached to one another so as to seal said narrow cavity extending below said living hinge and between said lower portions of said front and back walls.

3. The dispenser of claim 1 further comprising:
   interengaging means defined on said front and back walls at said upper portions thereof for making a releasable snap fit engagement of said lid with said back wall of said casing.

4. The dispenser of claim 3 wherein said interengaging means includes:
   a lip defined on a periphery of said upper portion of said front wall of said casing that forms said lid, said lip facing toward said upper portion of said back wall of said casing; and
   a recessed edge defined on a periphery of said upper portion of said back wall of said casing adjacent to said periphery of said upper portion of said front wall thereof such that when said lid is in said closed position said recessed edge is adapted to make said snap fit engagement with said lip of said lid.

5. The dispenser of claim 4 wherein said interengaging means further includes a protuberance formed on and extending upwardly from said recessed edge of said upper portion of said back wall of said casing, said protuberance being disposed behind said lip when said lid is in said closed position.

6. The dispenser of claim 1 wherein said aroma-producing means is a piece of absorbent material carrying an aroma-producing substance.

7. The dispenser of claim 6 wherein said upper and lower portions of said back wall of said casing have a plurality of interior positioning pins attached thereon and extending into said cavity and spaced apart so as to properly position said piece of absorbent material within said cavity.

8. The dispenser of claim 6 further comprising:
   a flat insert plate disposed within said narrow cavity of said casing and contacting an upper portion of said body of material, said insert plate partially exposing said upper portion of said body of material to the external environment when said lid is in said opened position.

9. The dispenser of claim 8 wherein said insert plate has a plurality of apertures for passage of said scent of said substance carried by said body of absorbent material to the external environment when said lid is in said opened position.

10. The dispenser of claim 9 wherein:
    said upper portion of said back wall of said casing has a pair of interior positioning pins attached thereon and extending into said cavity; and
    said insert plate has a pair of holes spaced apart from one another and alignable with said positioning pins to match and snugly receive said positioning pins of said upper portion of said back wall of said casing and thereby removably secure said insert plate to said upper portion of said back wall of said casing with said upper portion of said piece of material sandwiched therebetween such that said piece of material is exposed to the external environment substantially only through said apertures of said insert plate when said lid is in said opened position.

11. The dispenser of claim 1 wherein said lower-portion of said front wall of said casing has one of a plurality of pins or a plurality of receptacles attached on an interior surface thereof and spaced apart from one another along and extending outwardly past a peripheral rim on said lower portion of said front wall.

12. The dispenser of claim 11 wherein said lower portion of said back wall of said casing has the other of said plurality of pins or said plurality of receptacles attached on an interior surface thereof and spaced apart from one another along and extending outwardly past a peripheral rim on said front wall such that said pins fit into said receptacles so as to align and place said peripheral rims of said lower portions of said front and back walls in contact with one another.

* * * * *